United States Patent [19]

Kensey et al.

[11] Patent Number: 5,383,886
[45] Date of Patent: Jan. 24, 1995

[54] METHODS AND INSTRUMENTS FOR PERFORMING MEDICAL PROCEDURES PERCUTANEOUSLY WITHOUT A TROCAR

[75] Inventors: Kenneth Kensey, Chester Springs; Harold Clupper, West Chester, both of Pa.

[73] Assignee: Kensey Nash Corporation, Exton, Pa.

[21] Appl. No.: 959,857

[22] Filed: Oct. 13, 1992

[51] Int. Cl.⁶ .............................................. A61B 17/00
[52] U.S. Cl. ................................. 606/185; 128/898; 606/205
[58] Field of Search ............... 606/167, 184, 185, 205, 606/206, 207, 211; 128/745, 749, 898

[56] References Cited

U.S. PATENT DOCUMENTS

| | | |
|---|---|---|
| 37,023 | 11/1862 | Woolley . |
| 984,756 | 2/1911 | Frisch . |
| 1,573,681 | 2/1926 | Daireaux . |
| 1,600,225 | 9/1926 | Halpern . |
| 1,659,112 | 2/1928 | Littlejohn . |
| 2,025,345 | 12/1935 | Harris . |
| 2,934,070 | 4/1960 | Jerry . |
| 3,019,790 | 2/1962 | Militana . |
| 3,472,232 | 10/1969 | Earl . |
| 3,699,969 | 10/1972 | Allen . |
| 3,742,958 | 7/1973 | Rundles . |
| 3,828,791 | 8/1974 | Santos ................................ 606/207 |
| 3,840,008 | 10/1974 | Noiles . |
| 3,844,291 | 10/1974 | Moen . |
| 4,142,517 | 3/1979 | Stavropoulos et al. . |
| 4,354,491 | 10/1982 | Marbry . |
| 4,369,788 | 1/1983 | Goald ................................. 606/207 |
| 4,478,221 | 10/1984 | Heiss . |
| 4,517,965 | 5/1985 | Ellison . |
| 4,545,374 | 10/1985 | Jacobson . |
| 4,600,014 | 7/1986 | Beraha . |
| 4,608,982 | 9/1986 | Pollard . |
| 4,633,869 | 1/1987 | Schmieding . |
| 4,662,371 | 5/1987 | Whipple et al. . |
| 4,667,684 | 5/1987 | Leigh . |
| 4,681,123 | 7/1987 | Valtchev . |
| 4,716,901 | 1/1988 | Jackson et al. . |
| 4,721,116 | 1/1988 | Schintgen et al. . |
| 4,733,671 | 3/1988 | Mehl . |
| 4,763,669 | 8/1988 | Jaeger . |
| 4,790,329 | 12/1988 | Simon . |
| 4,815,467 | 3/1989 | Chestnut ........................... 606/185 |
| 4,836,205 | 6/1989 | Barrett . |
| 4,872,456 | 10/1989 | Hasson . |
| 4,877,026 | 10/1989 | de Laforcade . |

(List continued on next page.)

FOREIGN PATENT DOCUMENTS 3812165 10/1989 Germany ........................... 606/205

Primary Examiner—Tamara L. Graysay
Attorney, Agent, or Firm—Caesar, Rivise, Bernstein, Cohen & Pokotilow, Ltd.

[57] ABSTRACT

An instrument and method for performing some medical procedure in an interior portion of the body of a living being from outside the body of the being via a small percutaneous incision or puncture. The instrument includes a proximal portion, a distal portion, and a working head coupling to the proximal portion to be operated thereby. The proximal portion is arranged to be held outside the body of the being by the user of the instrument. The distal portion comprises a tip having a tissue engagement surface which is sufficiently blunt so that it does not present a hazard to internally located tissue, yet which will form at least a portion of the percutaneous incision or puncture. The distal portion of the instrument is arranged to be extended through the skin and underlying tissue, which is internally supported, e.g., insufflated, to form the percutaneous incision or puncture upon the application of pressure onto the instrument so that the working head passes through the incision or puncture into the interior portion without the use of a trocar. When in position the proximal portion of the instrument is operated to cause the working head to perform the procedure. When the procedure is finished the instrument is removed from the percutaneous incision or puncture, whereupon it seals itself, thereby obviating the need for suturing or other artificial seals.

6 Claims, 2 Drawing Sheets

U.S. PATENT DOCUMENTS

| | | | |
|---|---|---|---|
| 4,881,551 | 11/1989 | Taylor . | |
| 4,889,118 | 12/1989 | Schwiegerling | 606/108 |
| 4,907,599 | 3/1990 | Taylor . | |
| 4,917,100 | 4/1990 | Nottke . | |
| 4,924,878 | 5/1990 | Nottke . | |
| 4,953,558 | 9/1990 | Akerfeldt . | |
| 4,958,625 | 9/1990 | Bates et al. . | |
| 4,963,147 | 10/1990 | Agee et al. . | |
| 4,976,269 | 12/1990 | Mehl . | |
| 4,991,600 | 2/1991 | Taylor . | |
| 5,007,914 | 4/1991 | Schweigerling | 606/108 |
| 5,031,634 | 7/1991 | Simon | 128/754 |
| 5,036,860 | 8/1991 | Leigh et al. . | |
| 5,048,538 | 9/1991 | Terwilliger et al. . | |
| 5,066,288 | 11/1991 | Deniega et al. . | |
| 5,071,408 | 12/1991 | Ahmed | 606/108 |
| 5,078,724 | 1/1992 | Takase | 606/167 |
| 5,080,655 | 1/1992 | Haaga . | |
| 5,133,724 | 7/1992 | Wilson, Jr. et al. | 606/207 |
| 5,135,525 | 8/1992 | Biscoping et al. | 604/51 |
| 5,183,465 | 2/1993 | Xanthakos et al. | 604/108 |
| 5,192,293 | 3/1993 | Cartwright et al. | 606/172 |

U.S. Patent  Jan. 24, 1995  Sheet 1 of 2  5,383,886
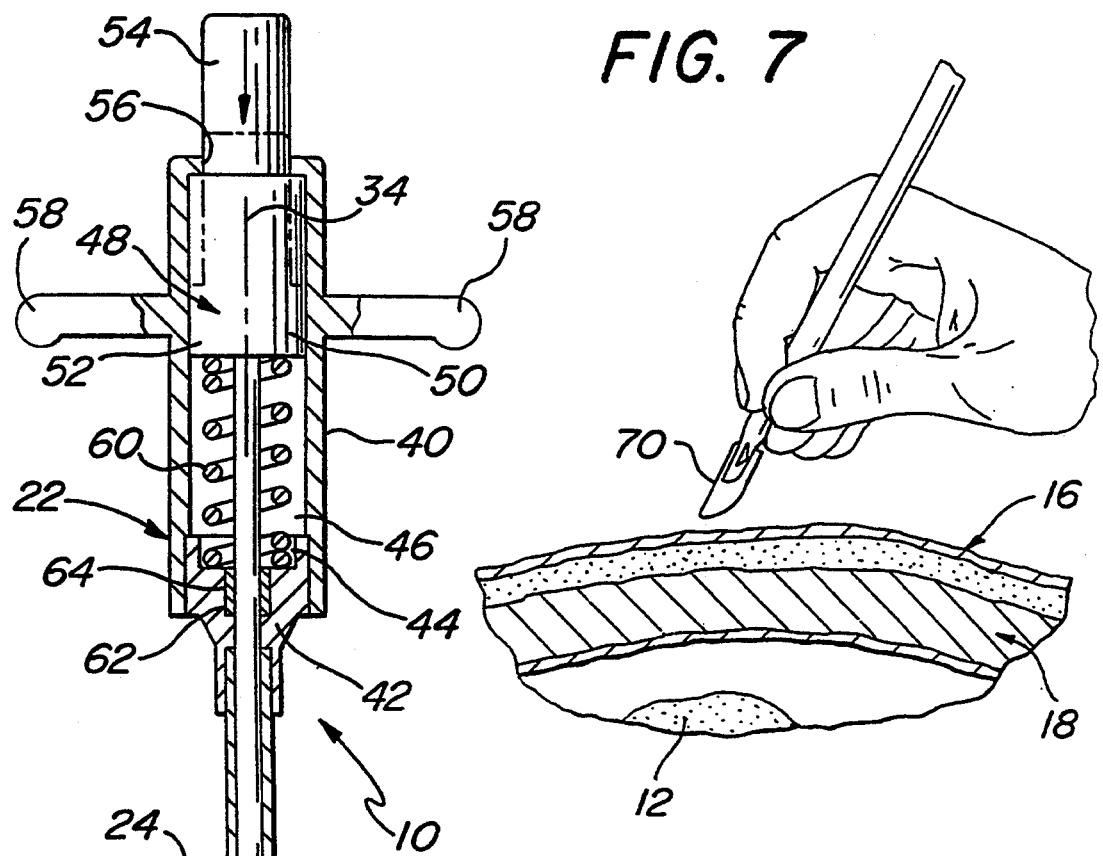
FIG. 1
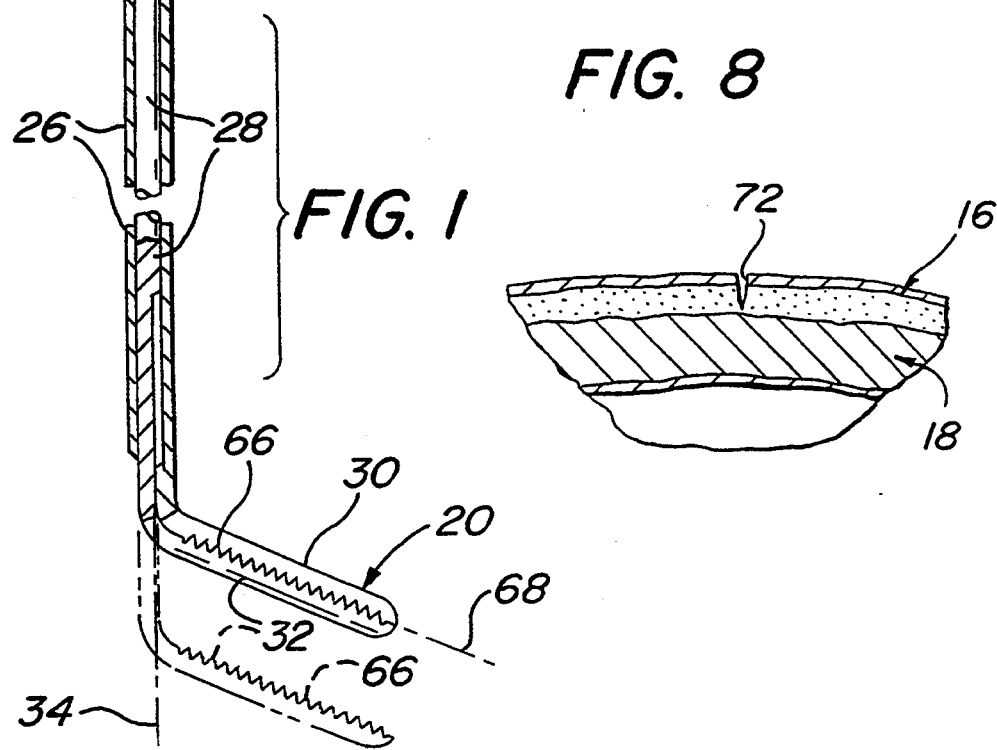
FIG. 7
FIG. 8

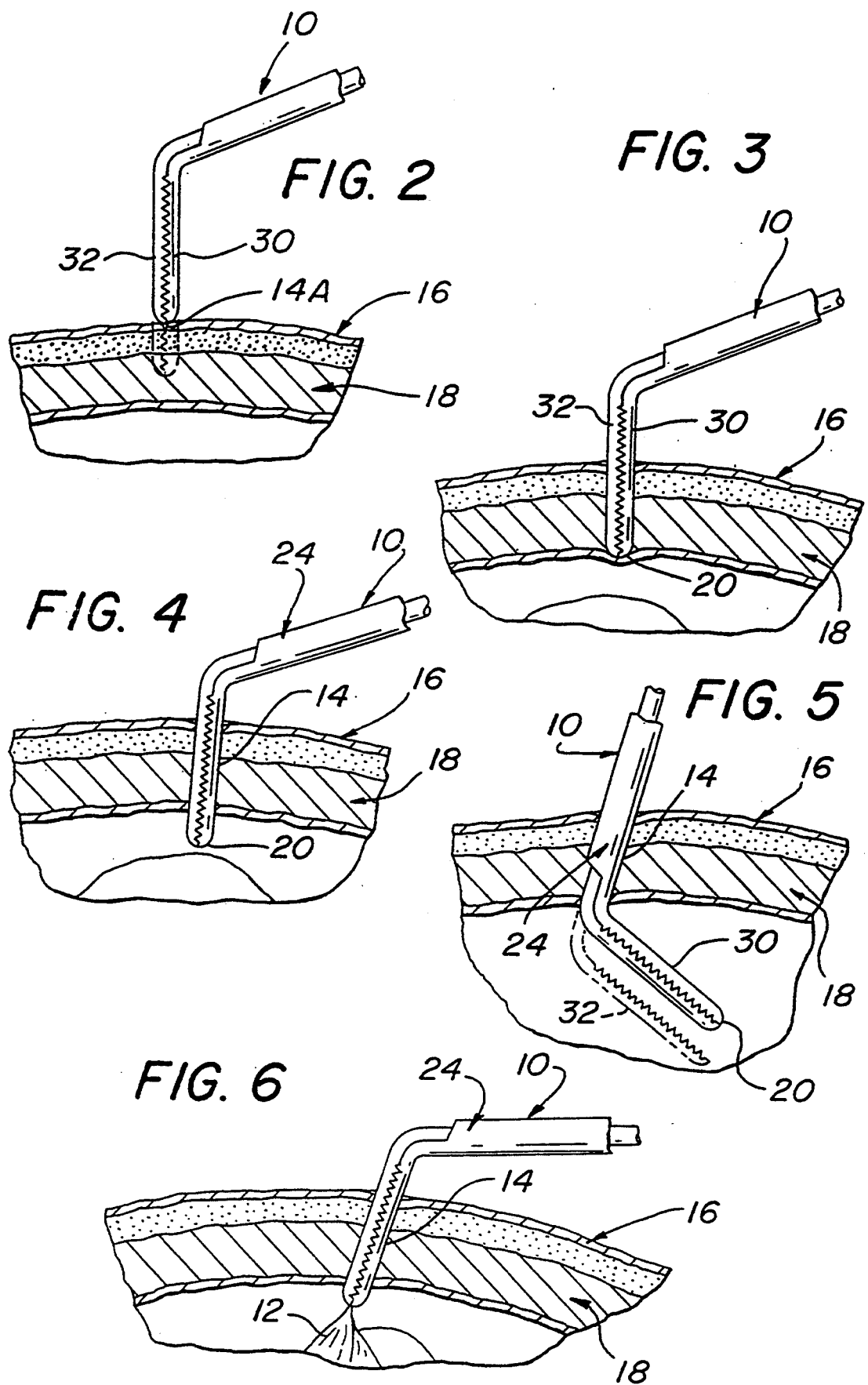

METHODS AND INSTRUMENTS FOR PERFORMING MEDICAL PROCEDURES PERCUTANEOUSLY WITHOUT A TROCAR

This invention relates generally to medical devices and methods of use, and more specifically to devices and methods of use for performing medical procedures within the body of a patient via a small percutaneous incision or puncture and without requiring the use of a trocar to provide access into the patient's body.

Various devices are commercially available for introduction through a trocar into the body of a being to effect some laparoscopic or endoscopic procedure. One typical type of device comprises grasper for grasping and positioning, e.g., reflecting, tissue within the patient's body. Such devices comprise an elongated body member having a distal end at which a pair of pivotable jaws are located and a proximal end at which a pair of pivotable actuating handles are located. The instrument is inserted within the patient's body through a conventional trocar until the pivotable jaws are located adjacent the tissue to be clamped. The actuating handles are then squeezed together to cause the jaws, which are coupled thereto, to grasp the tissue. Other types of trocar introduced devices used heretofore are staplers, biopsy devices, electrocautery devices, suturers, etc.

The patent literature includes various devices for to effect some laparoscopic, endoscopic, arthroscopic, or other minimally invasive surgery or procedure, e.g., U.S. Pat. Nos.: 4,662,371 (Whipple et al.); 4,763,669 (Jaeger); 4,872,456 (Hasson); 4,917,100 (Nottke); and 4,963,147 (Agee et al.).

Other medical instruments utilizing jaws or cutting blades are shown in U.S. Pat. Nos.: 984,756 (Frisch); 1,659,112 (Littlejohn); and 4,877,026 (Laforcade).

While the prior art devices may be suitable for their intended purposes, they never the less leave much to be desired from various standpoints. For example, instruments requiring the use of a trocar for percutaneous introduction typically require that the incision or puncture be sutured after the trocar has been removed. Obviously, this action is time consuming, relatively expensive, and wasteful of personnel resources. Moreover, the making of the incision or puncture sufficiently large for a conventional trocar is somewhat traumatic for the patient, particularly if multiple incisions or punctures are required to effect the percutaneous procedure.

In U.S. patent application Ser. No. 07/936,419, filed on Aug. 27, 1992, entitled Instruments And Methods For Performing Medical Procedures Via Small Percutaneous Incisions or Punctures Without Using A Trocar, which is assigned to the same assignee as this invention, and whose disclosure is incorporated by reference herein there is disclosed an claimed various devices and methods for effecting medical procedures via very small, self-sealing, percutaneous incisions or punctures without using a trocar to expedite the procedures, conserve medical resources, minimize trauma to the patient. To achieve that end the apparatus of that invention has a proximal portion and a distal portion, with the distal portion including a sharp piercing end for forming a small percutaneous incision or puncture to enable the distal portion be inserted into the being's body to a desired internal position without the use of a trocar or other introducing device. The distal portion of the apparatus is elongated and has a longitudinal axis. In one embodiment, an actuatable mechanism, e.g., a pair of moveable jaws, is located at the distal portion and is arranged to be pivoted outward laterally of the longitudinal axis for engagement with tissue located at the operative site to perform some operation, e.g., clamping. The actuatable mechanism is actuated by the proximal portion of the apparatus. In another embodiment, the jaws are permanently extended outward of the longitudinal axis. The piercing tip may take various forms. In one form it is pivotable to enable it to be moved from an extended position to a retracted position after it has pierced the skin and underlying tissue and is within the interior of the patient's body. In another form the piercing tip is removable so that it can be removed after it has pierced the skin and underlying tissue and is within the interior of the patient's body.

While the apparatus and methods of use of the invention of the aforementioned patent application are suitable for their intended purposes they still leave something to be desired from the standpoint of simplicity.

OBJECTS OF THE INVENTION

Accordingly, it is a general object of this invention to provide methods and instruments which overcomes the disadvantages of the prior art.

It is a further object of this invention to provide methods and apparatus for accomplishing medical procedures by piercing through internally supported tissue of a patient to form one or more percutaneous incisions or punctures which are very small to minimize trauma to the patient.

It is a further object of this invention to provide methods and apparatus for accomplishing medical procedures by piercing through internally supported tissue of a patient to form one or more percutaneous incisions or punctures which are sufficiently small that they need not be sutured or otherwise artificially sealed after the apparatus has been removed therefrom.

It is a further object of this invention to provide methods and apparatus for accomplishing medical procedures by piercing through internally supported tissue of a patient to form one or more percutaneous incisions or punctures which are sufficiently small that they seal themselves after the apparatus has been removed therefrom.

SUMMARY OF THE INVENTION

These and other objects of this invention are achieved by providing methods and apparatus for performing various types of medical procedures in an interior portion of the body of a living being from outside the body of the being via a small percutaneous incision or puncture and without using a trocar or other means to hold the incision or puncture open.

The apparatus is an instrument having a proximal portion, a distal portion, working means, and coupling means. The proximal portion of the instrument is arranged to be held outside the body of the being. The distal portion of the instrument comprises a tip including a tissue engagement surface arranged to engage and be extended through the skin and underlying internally supported tissue of the being to form the percutaneous incision or puncture upon the application of pressure to the instrument so that the distal portion and the working means passes through the incision or puncture into the interior portion without the use of a trocar or other introducing means and so that the working means is located at a desired position within the interior portion of the being's body.

The surface of the piercing tip is sufficiently blunt so as not to present a hazard to tissue or organs located within the interior portion of the being's body. The coupling means is coupled to the working means and to the proximal portion to effect the operation of the working means via the proximal portion.

In accordance with one method of this invention one brings the tip of the apparatus into engagement with the skin over said interior portion of the patient's body and applies pressure thereto to pass through the skin and underlying tissue to form the percutaneous incision or puncture. Then, the distal portion and the working means of device is passed through the incision or puncture without using a trocar or any other introducing means so that the working means is located at a desired position within the patient's body. Then one operates the proximal portion of the apparatus so that the working means performs the desired procedure. Once that has been accomplished one then withdraws the distal portion and the working means of the apparatus out of the interior portion of the patient's body and out of the percutaneous incision or puncture.

If necessary, or desirable, the skin of the patient may be cut or nicked slightly by some means, e.g., a scalpel, to act as a starting point for the percutaneous incision or puncture and to facilitate the passage of the tip of the apparatus through the skin to form the percutaneous incision or puncture.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a longitudinal sectional view of one instrument constructed in accordance with the subject invention for carrying out a method in accordance with the subject invention;

FIGS. 2-6 are illustrations showing the sequence of use of the instrument of FIG. 1 for effecting the reflection of a lobe of the liver to expose the gall bladder; and FIGS. 7 and 8 are illustrations, similar to that of FIGS. 2-6, but showing two preparatory steps for accomplishing the method of this invention.

DETAILED DESCRIPTION OF THE PREFERRED EMBODIMENT

Referring now in greater detail to the various FIGURES of the drawings wherein like reference characters refer to like parts there is shown in FIG. 1 an instrument for accomplishing a method of this invention. In particular, the instrument 10 is arranged to be extended, without use of any trocar or similar device, through the skin and underlying internally supported tissue of the body of a living being to perform some procedure therein, e.g., for grasping internal tissue to hold it in place or reflect it to a different position during endoscopic, laparoscopic, arthroscopic, or other similar percutaneous procedures.

In fact, the instrument 10 is arranged to form the percutaneous incision or puncture, with the size of the percutaneous incision or puncture being sufficiently small that it seals itself upon removal of the instrument from it. To that end the instrument 10 includes an elongated portion (to be described later) of very small cross sectional area for passing through the percutaneous incision or puncture formed by the instrument so that the distal end of the elongated portion of the instrument is located within the body of the patient at a desired situs.

The distal portion of the instrument is in the form of a pair of jaws (also to be described later) which conjoin so that the surfaces of their distal free ends together form a tissue engagement surface in the form of a piercing tip 20. The piercing tip 20 is arranged to pierce through the skin and underlying tissue to form the percutaneous incision or puncture. The jaws extend outward of the longitudinal axis of the instrument for grasping adjacent internal tissue, yet do not interfere with the passage of the elongated portion of the instrument through the percutaneous incision or puncture to the operative situs.

It must be pointed out at this juncture that the instrument 10 disclosed and described herein is merely exemplary of various types of instruments which can be constructed in accordance with the teachings of this invention. Thus, instruments can be constructed for effecting other types of procedures, such as resecting, ablating, cauterizing, suturing, stapling, etc., which are to be carried out through a very small percutaneous incision or puncture in order to minimize patient trauma and to facilitate healing.

The instrument 10 of this invention is similar to one of the instruments disclosed in the aforementioned patent application, except for the construction of the means which forms the percutaneous incision or puncture, i.e., the piercing tip 20.

In the illustrations of FIGS. 2-8 there is shown the distal end of the instrument 10 when it is used to reflect a lobe of a patient's liver 12 (FIG. 6) via a percutaneous incision or puncture 14 extending through the skin 16 and underlying tissue 18. In order to expedite the instrument's passage through the skin 16 and underlying tissue 18 to form the small percutaneous incision or puncture 14, such tissue should be supported internally. In cases where the instrument 10 has to extend into the abdomen the internal support for the tissue to be pierced can be readily achieved by insufflating the abdomen with a gas, as is conventional during laparoscopic surgery today. In cases where the surgery is to be performed within the chest, insufflation or other artificial support should not be necessary since the ribs should provide adequate internal support to enable the instrument to form the percutaneous incision or puncture between adjacent ribs.

Referring now to FIG. 1 it can be seen that the proximal portion of the instrument 10, basically comprises housing or body portion 22 from which an intermediate portion in the form of an elongated tubular sleeve assembly 24 extends. The sleeve assembly comprises an elongated sleeve 26, and an elongated rod or shaft 28 slidably mounted therein. The sleeve assembly 24 may be straight (as shown) or may be curved. In any case the distal end portion of the sleeve 26 includes an angularly oriented extension forming a jaw 30. In a similar manner the distal end portion of the shaft 28 includes an angularly oriented extension forming a jaw 32. The jaws make up the instrument's working means and are arranged to be slid with respect to each other parallel to the longitudinal axis 34 of the sleeve and rod so that then can be opened and closed.

It must be pointed out at this juncture that the use of the term "axis" in this application is in the broadest possible sense and context, and, hence, is not limited to a straight line, but can be a line of any shape, e.g., a curved line, since the sleeve assembly 24 need not be straight.

When the jaws 30 and 32 are completely closed, such as shown by the full lines in FIG. 1, they abut each other, whereupon the outer periphery of the conjoined jaws is substantially circular and of very small cross sectional area, e.g., the outside diameter of which is 0.109 inch (2.77 mm) or less. Moreover the distal end of each jaw is somewhat rounded, so that when the jaws are conjoined they form the heretofore identified piercing tip 20. It is in the conjoined jaw configuration that the instrument 10 is used to pierce through the patient's skin 16 and underlying tissue 18 to locate its jaws 30 and 32 within the body of the patient at the desired situs (as will be described later).

In accordance with one aspect of this invention the rounded surface of the tip 20 is sufficiently pointed or tapering that it can pass through the skin 16 and underlying internally supported tissue 18 upon the application of a manual force by the surgeon to the instrument, yet is sufficiently blunt that it will not pose a hazard to internally located tissue, e.g., tissue within the insufflated abdomen.

In accordance with a preferred embodiment of this invention the outside diameter of the sleeve assembly 24 is very small, e.g., 0.109 inch (2.77 mm) or less, so that the formation of the percutaneous puncture or incision 14 produced by the instrument 10 is very small and self-sealing. By self-sealing it is meant that the puncture or incision will close and seal itself almost immediately after the instrument is withdrawn therefrom and without requiring suturing, taping, or other artificial sealing means.

The body 22 of the instrument 10 basically comprises a hollow cylindrical housing 40 fixedly connected by a connector 42 to the proximal end of the sleeve 26. The housing 40 has a cylindrical interior cavity 46 in which a plunger assembly 48 is located. The plunger assembly is connected to the proximal end of the shaft 28 and serves as the means for sliding the shaft 28 within the sleeve 26 along axis 34 to effect the opening and closing of the jaws 30 and 32.

The plunger assembly 48 basically comprises a rod-like plunger element 50 having a distal end 52 at which the proximal end if the shaft 28 is fixedly secured. The outside diameter of the plunger element 50 is just slightly less than the inside diameter of the hollow interior 46 of the housing so that the plunger element can be slid longitudinally therethrough. The proximal end of the plunger element 50 is in the form of a cap or button 54 which extends through an opening 56 at the proximal end of the housing 40.

The housing 40 includes a pair of tabs 58 projecting perpendicular to the longitudinal axis 34 of the instrument 10. A helical compression spring 60 is located within the hollow interior 46 of the housing 40 interposed between the distal end 52 of the plunger element 50 and an annular recess 44 in the inner surface of the connector 42. The spring 60 surrounds the proximal portion of the shaft 28 and serves to bias the plunger element 50 toward the full line position shown in FIG. 1. In this orientation the jaws 30 and 32 of the instrument 10 are fully closed and the instrument arranged to form the percutaneous incision or puncture 14.

In order to center the shaft 28 within the sleeve 26 and to facilitate its sliding action within the sleeve 26, a linear bushing 62 is located within a second annual recess 64 in the connector 42.

The jaw 30 comprises an angular extension of the distal end of the sleeve 26. The angular extension is slightly thicker than the thickness of the sleeve's sidewall and includes an inner surface 66 having a plurality of transversely extending serrations to form a good tissue grabbing surface. The jaw 32 comprises an extension of the shaft 28 and also includes a serrated inner surface 66.

The cross sectional profile of each of the jaws taken perpendicularly to their longitudinal axis 68 is generally semicircular so that when the jaws are fully closed, i.e., when their serrated inner surfaces 66 abut, the profile of the conjoined jaws 30 and 32 is circular and of very small cross sectional area, e.g., 0.109 inch (2.77 mm) or less, while the conjoined free distal end surfaces of the jaws form the heretofore described tapered or rounded piercing tip 20.

The operation of the instrument 10 to effect reflection of some internally located tissue, e.g., a lobe of the liver 12, will now be described with reference to FIGS. 2–8. To accomplish that operation the skin 16 and underlying tissue 18 of the patient's abdomen and which are located over the patient's liver 12 is preferably insufflated with any suitable gas. Once this has been accomplished the surgeon grasps the instrument 10 in one hand, with his/her thumb disposed on the cap 54 and with his/her forefinger and index finger disposed on the respective extending tabs 58. The instrument 10 is now ready to form the percutaneous incision or puncture 14 into the patient's abdomen. To that end the surgeon brings the tip 20 of the instrument 10 into engagement with the patient's skin 16 located over the operative internal situs, e.g., the insufflated abdomen, and orients the instrument so that the conjoined angularly extending jaws are oriented in the desired direction, e.g., are perpendicular, with respect to the patient's body, such as shown in FIG. 2. The surgeon then pushes on the instrument so that the perpendicularly extending portion of the instrument is directed inward, i.e., toward the patient's abdomen. This action causes the piercing tip 20 to pierce into and through the skin and the underlying tissue, as shown by the phantom lines in FIG. 2 and the solid lines in FIG. 3, until the tip 20 enters into the abdomen, as shown in FIG. 4, whereupon a small percutaneous incision or puncture 14 is formed.

Once the conjoined angularly extending jaws are fully within the insufflated abdomen the instrument 10 is then oriented as shown in FIG. 5 so the contiguous longitudinally extending portion of the sleeve assembly 24 passes into the percutaneous incision or puncture 14. Continued inward pushing on the instrument forces more of the sleeve assembly through the puncture 14 until the conjoined jaws 30 and 32 are at the desired internal position. This procedure can be monitored visually or electronically via any conventional means, e.g., a laparoscope.

Once the jaws 30 and 32 are free of the percutaneous incision or puncture, i.e., are within the abdomen, and adjacent the tissue to be reflected, they may be opened to grasp that tissue therebetween. To accomplish that result the surgeon applies thumb and finger pressure to the thumb cap 54 and finger tabs 58, respectively, to move the plunger element 50 further into the housing. The movement of the plunger causes the concomitant movement of the shaft 28 within the sleeve 26 against the bias force produced by the compression spring 60. This action has the effect of moving the jaw 32 away from the jaw 30, thereby opening the jaws, like shown by the phantom lines in FIG. 5, whereupon the instrument can be manipulated so that a portion of the desired lobe of the liver be located between the open jaws.

In order to grasp that tissue the surgeon merely has to release the thumb pressure on the cap, whereupon the spring 60 carries the plunger element and the shaft 28 in the proximal direction until the jaws 30 and 32 close on the interposed tissue 12. That tissue can then be held in position or reflected, as shown in FIG. 6, depending upon the desires of the surgeon.

Once the laparoscopic procedure has been accomplished, the surgeon may release the grasped tissue by again applying thumb pressure on the thumb cap 54 while his/her fingers hold the tabs 58. After the tissue is released the instrument 10 can be readily slid out of the percutaneous incision or puncture 14, so that the incision or puncture immediately closes and seals itself.

In some cases in order to expedite the formation of the percutaneous incision or puncture 14, e.g., if the instrument utilized does not include a tip which is suitable for piercing through the skin by itself without the application of undue force, the surgeon may utilize a conventional scalpel 70 (or any conventional cutting or piercing means) to start the percutaneous incision or puncture. This action is shown in FIG. 7. In particular, the surgeon can make a shallow cut or nick 72, of very short length (e.g., 1 mm), into the skin 16 but not through the underlying tissue 18. Then the piercing tip of the instrument to be used can be brought into contact with the nick 72 and pressure applied thereto via the instrument, whereupon the instrument's tip and contiguous portions will easily penetrate the underlying tissue to complete the formation of the percutaneous incision or puncture. The instrument may then be manipulated as described above so that its working (e.g., distal) end is at the desired internal position, whereupon the instrument may be operated to perform the desired procedure. After that has been accomplished the instrument may be withdrawn from the percutaneous incision or puncture, whereupon it will quickly seal itself.

Without further elaboration the foregoing will so fully illustrate our invention that others may, by applying current or future knowledge, adopt the same for use under various conditions of service.

What is claimed is:

1. A method for performing a medical procedure in an interior portion of the body of a living being from outside the body of said being via a small percutaneous incision or puncture by the use of an instrument, said instrument having a proximal portion, an intermediate portion, and a distal portion, said distal portion comprising working means and a tip, said tip having a tissue engagement surface which is sufficiently blunt so as not to present a hazard to tissue or organs located within the interior portion of the being, said method comprising the steps ensuring that the skin and tissue over the interior portion is supported, bringing said tissue engagement surface into engagement with the skin over the interior portion and applying pressure thereto to pass through the skin and underlying tissue to form the percutaneous incision or puncture, moving said working means of said instrument directly through the percutaneous incision or puncture so that said working means is at a desired position within said interior portion of said being and with the tissue contiguous with the incision or puncture engaging portions of the instrument extending through the incision or puncture, operating said working means from outside the body of said being so that said working means performs said procedure, and then withdrawing said instrument out of said percutaneous incision or puncture, the incision or puncture being sufficiently small that it is quickly self-sealing after said distal portion of said instrument has been removed therefrom.

2. The method of claim 1 wherein said interior portion is insufflated to support said skin and tissue over said interior portion.

3. The method of claim 1 wherein said skin and tissue over said interior portion is supported by some naturally existing structure of the being's body.

4. The method of claim 1 additionally comprising the step of making a slight cut or nick into the skin of said being but not through said underlying tissue and thereafter bringing said tissue engagement surface into engagement with said cut and applying pressure to said instrument to start said percutaneous incision or puncture from said slight cut or nick.

5. The method of claim 4 wherein said slight cut is made by use of another device.

6. The method of claim 5 wherein said other device comprises a scalpel.

* * * * *